United States Patent
King et al.

(10) Patent No.: US 7,264,739 B2
(45) Date of Patent: Sep. 4, 2007

(54) DENDRIMER FLUID PURIFICATION METHOD

(75) Inventors: Joseph A. King, Wayzata, MN (US); John E. Hill, Plymouth, MN (US)

(73) Assignee: King Technology

( * ) Notice: Subject to any disclaimer, the term of this patent is extended or adjusted under 35 U.S.C. 154(b) by 0 days.

(21) Appl. No.: 11/343,287

(22) Filed: Jan. 30, 2006

(65) Prior Publication Data

US 2006/0157427 A1 Jul. 20, 2006

Related U.S. Application Data

(62) Division of application No. 10/393,903, filed on Mar. 24, 2003, now Pat. No. 7,048,864.

(51) Int. Cl.
*C02F 1/50* (2006.01)
(52) U.S. Cl. ............... 210/764; 422/28; 424/618; 426/322; 426/330.5; 426/532
(58) Field of Classification Search ............... 210/764
See application file for complete search history.

(56) References Cited

U.S. PATENT DOCUMENTS

| | | | | |
|---|---|---|---|---|
| 3,860,729 A * | 1/1975 | Strandskov et al. | ..... | 426/330.3 |
| 5,266,217 A * | 11/1993 | Roe et al. | .................... | 210/764 |
| 5,308,482 A * | 5/1994 | Mead | ......................... | 210/207 |
| 5,336,636 A * | 8/1994 | Burmer | ...................... | 438/675 |
| 6,217,892 B1* | 4/2001 | King | ........................ | 424/408 |
| 6,224,898 B1* | 5/2001 | Balogh et al. | .............. | 424/445 |
| 6,329,011 B1* | 12/2001 | Oita | .......................... | 426/599 |
| 6,417,339 B1* | 7/2002 | Wiessler et al. | ............ | 536/4.1 |
| 6,440,405 B1* | 8/2002 | Cooper et al. | ........... | 424/78.17 |
| 6,527,952 B1* | 3/2003 | King | ........................ | 210/205 |
| 6,551,609 B2* | 4/2003 | King | ........................ | 424/409 |
| 6,579,906 B2* | 6/2003 | Cooper et al. | .............. | 514/646 |
| 6,652,871 B1* | 11/2003 | King et al. | .................. | 424/407 |

\* cited by examiner

*Primary Examiner*—Peter A. Hruskoci
(74) *Attorney, Agent, or Firm*—Jacobson & Johnson

(57) ABSTRACT

A dendrimer complex comprising a dendrimer and an antimicrobial agent with the dendrimer complex placeable directly into a fluid to inhibit growth of microbes or rid the fluid of microbes. In a further embodiment of the invention the dendrimer complex is secured to a carrier, which is placed in a body of fluid and allowed to dispense the antimicrobial agent into the fluid. Once the antimicrobial agent is dispensed, the dendrimer complex can be removed and recycled to add functional groups to the dendrimer so that the dendrimer can be reused.

3 Claims, 1 Drawing Sheet

DENDRIMER FLUID PURIFICATION METHOD

CROSS REFERENCE TO RELATED APPLICATIONS

This application is a division of U.S. application Ser. No. 10/393,903 filed Mar. 24, 2003, now U.S. Pat. No. 7,048,864.

FIELD OF THE INVENTION

This invention relates generally to fluid purification such as by ridding fluids of microbial activity and, more specifically, to use of dendrimer complexes to rid fluids of unwanted microbial activity.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of dendrimer technology and particularly dendrimers are well known in the art. In general, a dendrimer is a large molecule having a sphere-like shape and includes a core with outer branches for holding functional groups.

Dendrimers are unique, highly branched, organic molecules that represent a breakthrough in polymer synthesis. Dendrimers are considered to be novel because of their size, shape, and physical or chemical properties. Dendrimers represent an example of synthetic organic molecules having uniform size and 3-dimensional structures. A promising feature of dendrimers is that they can be synthesized to have various internal structure and various surface properties. Because of the multiple reaction sites on the dendrimer molecules they can be combined with a number of different compounds.

Dendrimers are considered nanotechnology since the size of a dendrimer molecule is typically in the nanometer range. In general, the dendrimers are comprised of three components a) a core material; b) a highly-uniform branched polymers attached in step-wise layers to the core and c) a nano-scaled 3-dimensional surface structure, commonly spherical. While the synthesis of dendrimers is known, it is oftentimes difficult and time consuming, thus the cost of dendrimers can be relatively expensive costing thousands of dollars per pound. The technology and use of dendrimers remains limited at least partly due to the high costs of the dendrimers. However, various dendrimer patents and publications on dendrimers include laundry lists of proposed applications or uses for dendrimers.

An example of a proposed use of a dendrimer in "wound treatment" is shown in Balogh U.S. Pat. No. 6,224,898. Balogh et al discloses that an antimicrobial agent comprising a metal-containing compound is distributed on or in a dendrimer polymer for applying to a specific type of wound, namely, "burn wounds". Balogh et al states his "dendrimer silver nanocomposite" is applied to a wound by a spray or is applied to a cloth substrate and then applied to a wound. While Balogh et al. conducts tests he concludes that his antimicrobial agent is effective "in vitro" for treatment of wounds.

While the dendrimers generally do not have any antibacterial properties the Cooper et al. U.S. Pat. No. 6,440,405 discloses formation of a quaternary ammonium functionalized dendrimer that does derive its antibacterial properties from the dendrimer itself. In Publication No. US 2002/022012 Cooper et al. goes on to propose "surface treatments" using a dendrimer biocide-silver nanocomposite as an antimicrobial agent. Cooper et al. prepares his biocide-silver nanocomposite by reacting the dendrimer biocide disclosed in his U.S. Pat. No. 6,440,405 with a silver compound. Cooper et al. then incorporates his biocide-silver nanocomposite into various surface coatings to provide the coating or surface with antimicrobial activity. Cooper et al. points out the use of the dendrimer with biocide-silver nanocomposite as being effective against agents such as anthrax. Cooper et al. specifically points out the incorporation of his dendrimer silver nanocomposite into "protective coatings or paints, personal products such as cosmetics, industrial products, hospital products, and sanitation of swimming pools and spas." Cooper et al. goes on to point out that his dendrimer silver nanocomposite can be "immobilized onto the surface to create efficient antimicrobial surfaces for use as biomaterial, anti-fouling paints, and other similar devices." Thus, Cooper et al. teaches the use of the biocide-silver nanocomposite within the structure or some type of coating to make antimicrobial surfaces.

The Tomalia et al. U.S. Pat. No. 5,714,166 discloses the use of dendrimers for "pharmaceutical and agricultural applications" More specifically, Tomalia et al discloses dense star polymers can be associated with a bioactive agent, a diagnostic agent or a therapeutic/diagnostic agent. Tomalia et al. teaches the use of the dense star polymers in pharmaceutical and agricultural applications. He specifically points out the transporting of genetic material through a cellular member and into a cellular nucleus with a dendrimer polymer.

The Tomalia et al U.S. Pat. No. 4,507,466 discloses the uses of dendrimers for emulsfier for oil or water emulsions, as wet strength agents in the manufacture of paper and agents for modifying the viscosity in aqueous formations such as paints.

The Tomalia et al. U.S. Pat. No. 4,694,064 discloses the use of dendrimer in the production of molecular composites and as crystalline modifiers for polymeric materials.

In the above references it is evident that the dendrimers or dendrimer biocides have been combined with various biocidal agents to produce antibacterial products that can be incorporated into articles or coatings to rid surfaces of bacteria. In contrast, the present invention has found that one can incorporate dendrimers with an antimicrobial agent directly into a fluid to control microbial activity in the fluid in order to render the fluid safe for either consumption or recreational uses. In addition, the invention includes a fluid treatment method that permits one to rid or at least inhibit microbial growth in the fluid and when the dendrimer antimicrobial agent is spent permits one to remove and recycle the dendrimer for combining with fresh antimicrobial agents.

SUMMARY OF THE INVENTION

A dendrimer complex comprising a large scale molecule having an antimicrobial agent as a functional group with the dendrimer complex placeable directly into a fluid to rid the fluid of microbes. In a further embodiment of the invention the dendrimer complex is secured to a carrier, which is placed in a fluid and allowed to release the antimicrobial agent carried by the dendrimer directly into the fluid. Once the antimicrobial agent is spent, the dendrimer complex can be removed and recycled to add fresh functional groups to the dendrimer so that the dendrimer can be reused.

DESCRIPTION OF THE PREFERRED EMBODIMENT

Dendrimers are known in the art and generally comprise large sphere like molecules that have a core, a shell of internal cells and a shell of exterior cells with sites for functional groups. One of the functional groups used with dendrimers includes biocides, other include specific materials. An example of dendrimer with a silver complex is shown in the Balogh U.S. Pat. No. 6,224,898, which is incorporated herein by reference.

The present invention utilizes the dendrimer as a carrier for an antimicrobial agent to permit the dendrimer with the antimicrobial agent to be placed directly into a fluid environment or in a fluid, which requires purification for a variety of purposes including being consumed or used for recreational purposes. As used herein the term dendrimer describes a highly branched molecule having a number of sites for attaching functional groups thereto. A dendrimer complex describes a dendrimer with a functional group attached to the dendrimer. For example, a dendrimer silver complex refers to a dendrimer with silver secured to the dendrimer. Similarly, a dendrimer metal ion yielding complex refers to a dendrimer having a metal secured to the dendrimer with the metal releasing metal ions when the dendrimer metal ion yielding material comes into contact with a fluid, such as water. As used herein the term antimicrobial agent references to a material that kills or inhibits the growth of microbes including bacteria and other organisms.

Figure 1:
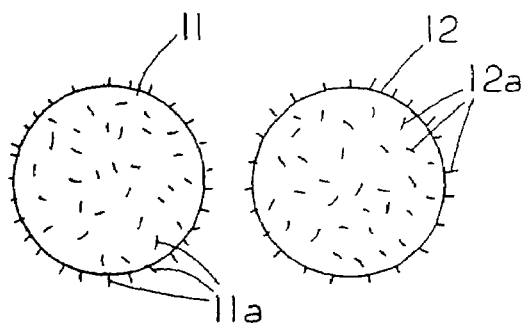
FIG. 1 schematically represents the two molecules of FIG. 1 with functional groups secured to the outer branches.

FIG. 1 schematically represents a first large scale spherical molecule 11 located proximate a second large scale spherical molecule 12. Located on spherical shaped molecule 11 are a set of sites 11a where functional groups can be attached. Similarly, reference numeral 12 designates a second spherical shaped molecule having a set of sites 12a for securement of a functional group thereto. FIG. 1 represents dendrimers in a generally pre active state.

Figure 1A:
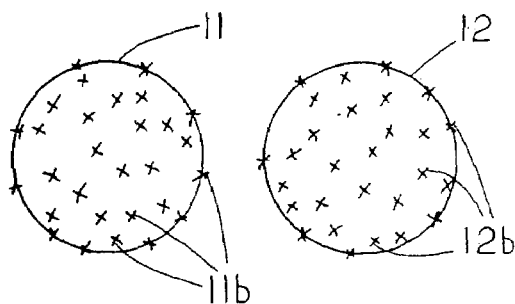
FIG. 1A schematically represents two molecules with sites for functional groups.

A reference to FIG. 1A illustrates the first spherical molecule 11 with a set of functional groups 11b secured to the sites 11a on molecule 11. Similarly molecule 12 contains a set of functional groups 12b secured to sites 12a on the molecule 12. In the present invention, an antimicrobial agent, which comprises the functional group, is secured to the dendrimer for purposes of controlling or killing microbes in a fluid. Examples, of specific types of materials useful in a fluid to kill microbes such as bacteria are metal ion yielding materials. One of the known metal ion yielding materials is silver chloride another is silver nitrate. Other metal ion yielding materials for use in water purification the for killing microbes can be a metal ion yielding material selected from the group consisting of zinc sulfate, zinc carbonate, zinc chloride, copper chloride, copper carbonate, copper sulfate, silver chloride, stannous chloride and stannic chloride. FIG. 1A schematically represents the dendrimer complex for killing microbes by release of the functional groups from the dendrimer molecule.

Figure 2:
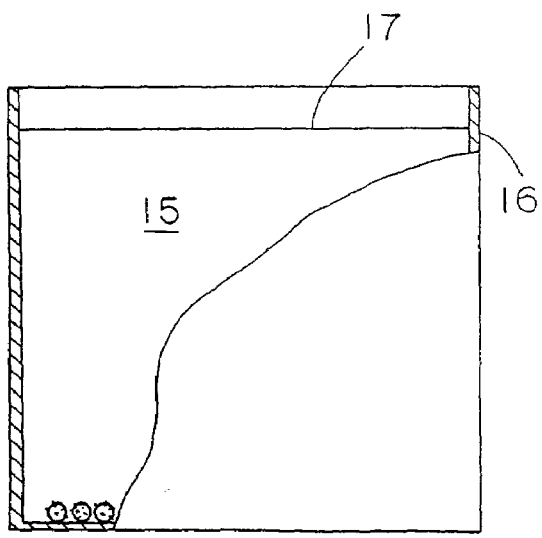
FIG. 2 shows a container containing a fluid with a dendrimer with functional groups schematically illustrated in the bottom of the container.

A part of the present invention is a method of disrupting microbe proliferation comprising securing a ion yielding material to a dendrimer and then bringing the dendrimer containing the ion yielding material in ion communication with a source of microbes, for example by placing the dendrimer with the ion yielding material into a body of fluid 15 as shown in FIG. 2 to allow the ions to come into the presence of the microbes. The body of fluid 15 can be recreational water such as found in a spa, hot tubs and pools or it can be fluid intended for consumption such as drinking water or it can be other types of fluids where the fluid requires purification such as by ridding or curtailing the microbial activity in the fluid. Thus, in one embodiment the present invention comprises a method of disrupting microbe proliferation by securing an antimicrobial agent to a dendrimer and immersing the dendrimer containing the antimicrobial agent in a fluid containing microbes, such as found in a body of water, to control microbial proliferation and thus render the water drinkable or suitable for recreational purposes.

In another method of fluid treatment one secures an antimicrobial agent to a dendrimer and places the dendrimer containing the antimicrobial agent into a fluid, which containing microbial activity, for sufficiently duration to rid the fluid of microbes. The fluid is not limited to water and could be fluids such as drinkable juices or the like. One then maintains the dendrimer containing the antimicrobial agent in the fluid for at least a time sufficient to control the microbial activity. The dendrimer containing the antimicrobial agent can then be removed and recycled by replacing the spent antimicrobial agent.

A further feature of the invention is that although the dendrimer containing the antimicrobial agent can be removed from the fluid one can also leave effective amounts of dendrimers containing antimicrobial agents in the fluids sufficient to kill the microbes in the fluids without having the antimicrobial agent or the dendrimer exceeding safe limits for human consumption or recreational use.

Another method of antiseptic treatment comprises forming a group of dendrimers and securing a antimicrobial agent to each of the group of dendrimers and bringing the group of dendrimers with the antimicrobial agent secured thereto into a source of microbial activity in a fluid so that the fluid must flow around the dendrimer containing the functional group. For example, one may want to kill microbes in body fluids including blood by incorporation the dendrimer with the antimicrobial agent into the fluid by running the blood through a screen having a dendrimer with an antimicrobial agent secured to the screen to thereby provide for on-the-go killing of microbes in the body fluid as the blood flows through the screen.

In another embodiment, the present invention comprises the method of microbial treatment in fluids comprising securing an antimicrobial agent such as a biocidal active agent to a dendrimer and applying the dendrimer with the biocidal active agent to a carrier, bringing the carrier with the biocidal active agent thereon into the presence of a microbial active site, such as in a fluid, and maintaining the carrier with the biocidal active agent in the presence of the microbial active site for sufficient time to at least inhibit microbial growth.

To determine the antimicrobial potential of various dendrimer complexes a dendrimer-silver complex was prepared using commercially available silver acetate with a dendrimer purchased from Dendritech, Inc. of Midland, Mich. After formation of the dendrimer-silver complex tests were performed to evaluate the antimicrobial activity using microorganisms of both *Pseudomonas aerligenosa* and *E. coli*. The test procedure is as follows:

EXAMPLE ONE

1. Prepare an inoculum of the test organism by streaking the entire surface of agar plates by the standard method for colony isolation, with *E. coli* (Nutrient Agar) and *Pseudomonas* (*Pseudomonas* Identification Agar). Incubate the streaked agar plates at 37° C. for approximately 18 hours.

2. Harvest all the growth on the test organism plates by flooding the plates with 9.0 ml of sterile distilled water per plate. Wash the harvested biomass by centrifugation for 1 hour at 3000 rpm, discarding the supernatant fluid, and resuspending the biomass in 9.0 ml of sterile distilled water. Resuspend harvested cell by vortex agitation for 1 minute.

3. Dilute 0.1 ml of the dendrimer-silver complex into 100 ml of 0.1% saline and sterile using a 0.45 micrometer filter.

4. Dispense 9.8 ml of the diluted complex to sterile test tubes and inoculate with 0.2 ml of the washed test microorganism as described above and mix.

5. Incubate for 10 minutes and perform serial dilution's and dispense 0.2 ml of dilution to agar plates for microbial enumeration by the spread plate method. *E. coli* was cultivated on Nutrient Agar (NA) and *Pseudomonas* was cultivated on *Pseudomonas* Identification Agar (PIA)

6. Incubate agar plates overnight at 37° C. and perform enumeration on plates having between 30 to 300 colonies.

7. Determine antimicrobial activity by taking the log difference between an untreated control and a plate of the same dilution treated with the test nanocomposite.

Test Results

Based on enumeration by the spread plate method, the untreated *Pseudomonas* control plate contained $1.94 \times 10^7$ colony forming unit (cfu), equivalent to a $\log_{10}$ value of 7.29. The *Pseudomonas* plate treated with the dendrimer-silver complex contained $1.0 \times 10^5$ cfu, equivalent to a $\log_{10}$ value of 5. The $\log_{10}$ different after 10 minutes of treatment is 2.3 or more than 99% reduction in cell numbers between the control and the treated plate.

The untreated *E. coli* had $1.3 \times 106$ cfu and the *E. coli* treated with he nanocomposite had less than $1 \times 10^5$ for a log 10 reduction of at least 1.1 which is equivalent to a 90% reduction in cfu after 10 minutes.

In contrast, testing with silver ions alone requires at least one hour to obtain a 1 $\log_{10}$ reduction in cfu of the test organisms. Based on the test results it was concluded that silver in the form of dendrimer-silver complexes, when placed in a fluid environment, is substantially more active as an antimicrobial substance than silver ions alone, even though it is well known that the silver ions posses strong antimicrobial activity.

EXAMPLE TWO

A second sample of a dendrimer silver complex was tested against various concentrations of silver nitrate against both *E. coli* and *Pseudomonas aerugentoas*. The experiment was performed as follows:

1. Prepare an inoculum of the test organisms by streaking the entire surface of agar plates, by the standard method for colony isolation, with ether *E. coli* or *pseudomonas* aerugentoas. The plates were incubated at 370° C. for approximately 18 hours.

2. Harvest all the growth on the test organism plates by flooding the plats with 9.0 ml of sterile distilled water per plate. Wash the harvested biomass by centrifugation for 1 hour at 3000 rpm, discarding the supernatant fluid, and resuspending in 9.0 ml of sterile distilled water. Resuspend harvested cell by vortex agitation for 1 minute.

3. Inoculate test plates with 0.2 ml with the test organism prepare as described above.

4. Place sterile 6-millimeter blank paper Discs on test plates and saturate with 10 microliters of the test substances.

5. Incubate the plates for 24 hours at 370c and report results as the diameter of the zone of inhibition around the discs treated with the test substances. The results are summarized below:

TEST RESULTS

| Test Substance | *Pseudomonas* (diameter of inhibitory zone) | *E. Coli* (diameter of inhibitory zone) |
|---|---|---|
| 10.0% Silver Nitrate | 11 | 6 |
| 7.5% Silver Nitrate | 7 | 6 |
| 5.0% Silver Nitrate | 6 | 6 |
| 2.5% Silver Nitrate | 6 | 6 |
| 1.0% Silver Nitrate | 9 | 6 |
| 0.5% Silver Nitrate | 12 | 6 |
| Complex I | 11 | 10 |
| Complex I dialyzed | 17 | 8 |
| Complex II | 13 | 9 |
| Complex III | 18 | 10 |

The tests results show the diameter of the inhibitory zone in millimeters where the microbes were effectively destroyed. The tests reveled that the dendrimer silver complex has an enhanced antimicrobial activity when compared to silver nitrate as evidenced by the larger diameter inhibitor zones. The exact mechanism is not fully understood but reveals that the dendrimer silver complex not only has greater effectiveness in killing microbes in fluids than well known metal ion yielding compounds but also acts more quickly than other metal ion yielding compounds that yield the same ion.

Figure 3:
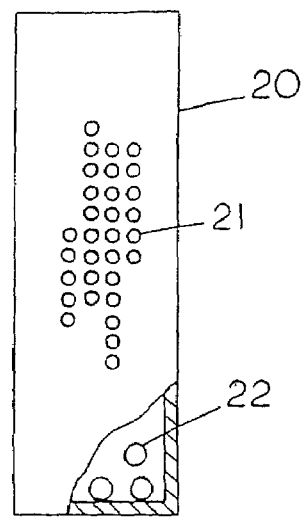
FIG. 3 is a dispenser containing a dendrimer with a antimicrobial agent for placing in a fluid.
Figure 5:
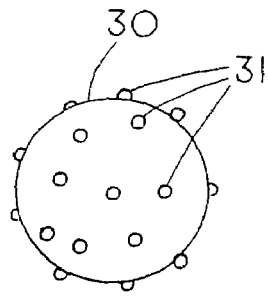
FIG. 5 shows a bead like object having a plurality of dendrimers with functional groups secured to the bead like object.

In the present invention various methods of deliver of the dendrimer complex containing the antimicrobial agent to the fluids are used. In one method the dendrimer complex containing the antimicrobial agent 31 is adhered to a small bead or fluid insoluble particle 30, such as shown in FIG. 5, or other particle carrier that has sufficient size to be retained within a dispenser as shown in FIG. 3. Dispenser 20 has a set of openings 21 which are smaller than the dendrimer containing material 22 within dispenser 20 to thereby retain the dendrimer containing material 22 therein. By confining the dendrimer complex 22 within the dispenser 20 the dendrimer complex 22 can be recycled and reused. The dendrimer complex 22 can be bonded to various material, such as illustrated in FIG. 5, to maintain the dendrimer in a condition where they can be retained and recovered for recycling. By adhering the dendrimer to a fluid insoluble carrier one can maintain the dendrimer in the fluid for purposes of fluid purification and then remove the dendrimer for recycling of the dendrimer.

Figure 4:
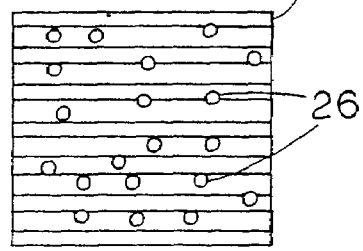
FIG. 4 shows a carrier such as a grid or fabric with dendrimers with functional groups secured to the carrier.

FIG. 4 shows another method, wherein the dendrimer is adhered to a larger structure such as some type of flow through member 25 that comes into contact with the fluid. For example, the dendrimer silver complex 26 can be placed on a flow through carrier such as a filter, a cloth, a membrane or other porous material or non porous material arranged to permit fluid to flow therethrough, such as illustrated in FIG. 4. A flow through carrier allows the dendrimer complex to come into direct contact with the fluid to be treated by flowing the fluid through the carrier. Although flowing the fluid through the carrier one can also immerse the carrier in the fluid. For example, placement of a carrier such as membrane or a fabric directly into a body of fluid such as water permits the dendrimer to yield the antimicrobial agent to attack the microbes in the fluid as the fluid flows through the carrier.

In still another method the dendrimer antimicrobial complex is placed directly in the fluid to be treated without adhering the dendrimer antimicrobial complex to a carrier. The dendrimer antimicrobial complex is useful in direct treatment all types of fluids including body fluids, recreational fluids and drinking fluids. As the dendrimers lacks any known appreciable toxicity the incorporation and the presence of the dendrimers in fluids, even those which are ingested by humans, is possible. In addition, the amount of measurable metal ions present in the fluids that is sufficient to control microbes can actually be less than the amount of measurable ions present with a conventional non-dendrimer compounds that also yield metal ions. The greater efficacy of the metal ions deliverable from a dendrimer as opposed to a non-dendrimer enables the use of metal ions for antimicrobial purposes that might be effective in killing microbes but could not be used because it requires antimicrobial levels in the fluid that would exceed safe human levels.

Thus the present invention includes a method of disrupting microbe proliferation securing a ion yielding material, such as a metal, to a dendrimer, bringing the dendrimer containing an ion yielding material in ion communication with a source of microbes in a fluid to control microbial proliferation therein.

The present invention also comprises a method of disrupting microbe proliferation securing an antimicrobial agent to a dendrimer, bringing the dendrimer containing the antimicrobial agent into proximity of a fluid containing microbes and maintain the dendrimer containing the antimicrobial agent in the fluid to control microbial proliferation in the fluid.

The invention includes a method of killing bacteria in a body of water applying a dendrimer containing a water purification material such as a bactericide to a carrier, placing the carrier with the dendrimer by immersing the carrier with the dendrimer containing the water purification material in a body of water and allowing water to contact the dendrimer containing the water purification material such as a bactericide to release the bactericide therefrom to kill bacteria in the body of water. In this method the dendrimer can be removed from the body of water after release of the water purification material and a fresh water purification material is releasable secured to the dendrimer followed by placing the dendrimer with the fresh water purification material back into the body of water to continue the water purification thereof. While a water purification material is attached to the dendrimer includes antimicrobial agents such as bactericides other water purification materials such as clarifiers can also be secured to the dendrimer to enable one to deliver the water purification materials to the fluids. If desired at least two water purification materials such as two different antimicrobial agents can be secured to the dendrimer to provide a wider range of effectiveness.

Thus the method of applying dendrimer containing a water purification material can be placed in recreational waters such as found in a spa, a pool or a hot tub. A use of the dendrimer with antimicrobial properties in drinkable fluids such as fruit juices functions to rid the juices of harmful microbes.

A further feature of the dendrimer complex, for example the dendrimer silver complex is even though heavy metals such as silver are considered toxic in excess of 100 ppb one can use the dendrimer silver complex to kill microbes in the water yet not have the level of heavy metal considerably below the considered toxic levels simply because of the antimicrobial efficiency of the dendrimer silver complex is more effective at lower concentrations.

We claim:

1. A method of disrupting microbe proliferation comprising;
   securing a ion yielding material to a dendrimer complex;
   placing the dendrimer complex containing the ion yielding material directly into a fluid to be treated without adhering the dendrimer complex to a carrier, to bring the dendrimer complex in ion communication with a source of microbes in a fluid to control microbe proliferation.

2. A method of disrupting microbe proliferation comprising:
   securing an antimicrobial agent to a dendrimer to form a dendrimer complex;
   placing the dendrimer complex containing the antimicrobial agent on to a flow through carrier and immersing the flow through carrier into a fluid containing microbes; and
   maintaining the dendrimer complex containing the antimicrobial agent immersed in the fluid to control microbial proliferation in the fluid.

3. A method of killing bacteria in a body of water comprising:
   applying a dendrimer containing a bactericide to a flow through carrier;
   placing the carrier with the dendrimer in direct contact with a body of water; and
   allowing the body of water to flow through the dendrimer containing a bactericide carrier to release the bactericide therefrom to kill a bacterium in the body of water.

* * * * *